United States Patent
Baust et al.

(10) Patent No.: US 7,416,548 B2
(45) Date of Patent: *Aug. 26, 2008

(54) CRYOGENIC SYSTEM

(75) Inventors: John G. Baust, Candor, NY (US); Roy Cheeks, Harpers Ferry, WV (US)

(73) Assignee: Endocare, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/688,007

(22) Filed: Mar. 19, 2007

(65) Prior Publication Data

US 2007/0213699 A1 Sep. 13, 2007

Related U.S. Application Data

(63) Continuation of application No. 10/478,937, filed as application No. PCT/US02/17104 on May 31, 2002, now Pat. No. 7,192,426.

(60) Provisional application No. 60/294,256, filed on May 31, 2001.

(51) Int. Cl.
*A61B 18/02* (2006.01)
*F17C 13/00* (2006.01)

(52) U.S. Cl. .............. 606/20; 606/21; 606/22; 606/25; 62/50.6

(58) Field of Classification Search ........... 606/20–26; 62/50.6
See application file for complete search history.

(56) References Cited

U.S. PATENT DOCUMENTS

| | | | |
|---|---|---|---|
| 4,345,598 A | 8/1982 | Zobac | |
| 4,472,946 A | 9/1984 | Zwick | |
| 4,499,737 A | 2/1985 | Binnig | |
| 4,860,545 A | 8/1989 | Zwick | |
| 4,946,460 A | 8/1990 | Merry | |
| 5,254,116 A | 10/1993 | Baust | |
| 5,257,977 A | 11/1993 | Eshel | |
| 5,334,181 A | 8/1994 | Rubinsky | |
| 5,400,602 A | 3/1995 | Chang | |
| 5,573,532 A | 11/1996 | Chang | |
| 5,916,212 A | 6/1999 | Baust | |
| 5,957,963 A | 9/1999 | Dobak | |
| 6,589,234 B2 | 7/2003 | Lalonde | |
| 7,192,426 B2 * | 3/2007 | Baust et al. | 606/20 |

* cited by examiner

*Primary Examiner*—Lee S Cohen
(74) *Attorney, Agent, or Firm*—Lawrence N. Ginsberg

(57) ABSTRACT

A cryosurgical system and method for supplying cryogen to a probe. The system including a container filled with cryogen and having bellows of a pump submerged within said cryogen. Conduits fluidly interconnect the bellows and a probe that is outside the container to permit the cryogen to be forced from the bellows to the probe upon activation of pump. A pressure relief valve is fluidly coupled to the conduits and positioned between the bellows and the probe. After initially forcing cryogen to the probe at a pressure that establishes a colligative-based sub-cooling of the liquid cryogen, the pressure relief valve is activated to lower the pressure of the cryogen to a running pressure.

5 Claims, 5 Drawing Sheets

CRYOGENIC SYSTEM

CROSS REFERENCE TO RELATED APPLICATIONS

This is a continuation of U.S. Ser. No. 10/478,937 entitled Cryogenic System, filed May 14, 2004, now U.S. Pat. No. 7,192,426, which claims the benefit of PCT Application No. PCT/US02/17104, filed May 31, 2002, which claims the benefit of U.S. Provisional Application Ser. No. 60/294,256, filed on May 31, 2001. The entire contents of U.S. Ser. No. 10/478, 937, PCT Application No. PCT/US02/17104 (WO 02/096, 270), and U.S. Ser. No. 60/294,256 are incorporated herein by reference thereto.

BACKGROUND OF THE INVENTION

1. Field of the Invention

The present invention relates to a cryogenic system. More specifically, illustrative embodiments of the present invention relate to a cryogenic system for use in cryosurgical procedures.

2. Description of the Related Art

The distribution of boiling (liquid) cryogens, such as liquid nitrogen, is problematic due to the parasitic heat load provided by a cryosurgical device's plumbing or transport circuit, which is maintained at ambient temperature. Pre-cooling the plumbing circuit, even if adequately insulated, causes two-phase flow (liquid-gas mixtures), cryogen boil-off, and choking flow due to gas expansion in the transport circuit. As a result, target temperatures at the distal end of the flow path (i.e., cryoprobe tip) are not reached for many minutes.

Some prior cryogenic systems and devices are disclosed in U.S. Pat. No. 4,345,598 to Zobac et al.; U.S. Pat. No. 4,472, 946 to Zwick; U.S. Pat. No. 4,860,545 to Zwick et al.; U.S. Pat. No. 4,946,460 to Merry et al.; U.S. Pat. No. 5,254,116 to Baust et al.; U.S. Pat. No. 5,257,977 to Eshel; U.S. Pat. No. 5,334,181 to Rubinsky et al.; U.S. Pat. No. 5,400,602 to Chang et al.; U.S. Pat. No. 5,573,532 to Chang et al.; and U.S. Pat. No. 5,916,212 to Baust et al., the entire contents of each being hereby incorporated herein by reference thereto, respectively.

SUMMARY OF THE INVENTION

The present invention can be embodied in a cryosurgical system, comprising a container having cryogen within the container; a pump having a piston submerged within the cryogen; a probe outside the container for use in cryosurgical procedures; a system of conduits fluidly interconnecting the piston and the probe permitting the cryogen to be forced from the piston to the probe upon activation of the piston; and a pressure relief device fluidly coupled to the systems of conduits and positioned between the bellows and the probe.

The present invention may also be embodied in a pump assembly for a cryosurgical system, comprising a driving mechanism coupled to an elongated drive shaft; a bellows coupled to the drive shaft and adapted to be submersed in cryogen, the bellows formed from metal; a one-way inlet valve fluidly coupled to the bellows; and a one-way outlet valve fluidly coupled to the bellows.

The present invention may also be embodied in a method of delivering cryogen to a surgical device, comprising providing a container having cryogen within the container; providing a pump having a piston within a cylinder and submerged within the cryogen; providing a surgical instrument outside the container for use in cryosurgical procedures; providing a system of conduits fluidly interconnecting the piston and the surgical instrument permitting the cryogen to be forced from the piston to the probe upon activation of the piston; providing a pressure relief device fluidly coupled to the systems of conduits and positioned between the bellows and the probe; activating the piston to pull cryogen within the cylinder; activating the piston to push the cryogen from the cylinder to the surgical instrument at an initial predetermined pressure.

Other aspects, features, and advantages of the present invention will become apparent from the following detailed description of the illustrated embodiments, the accompanying drawings, and the appended claims.

DETAILED DESCRIPTION OF THE INVENTION

Figure 1:
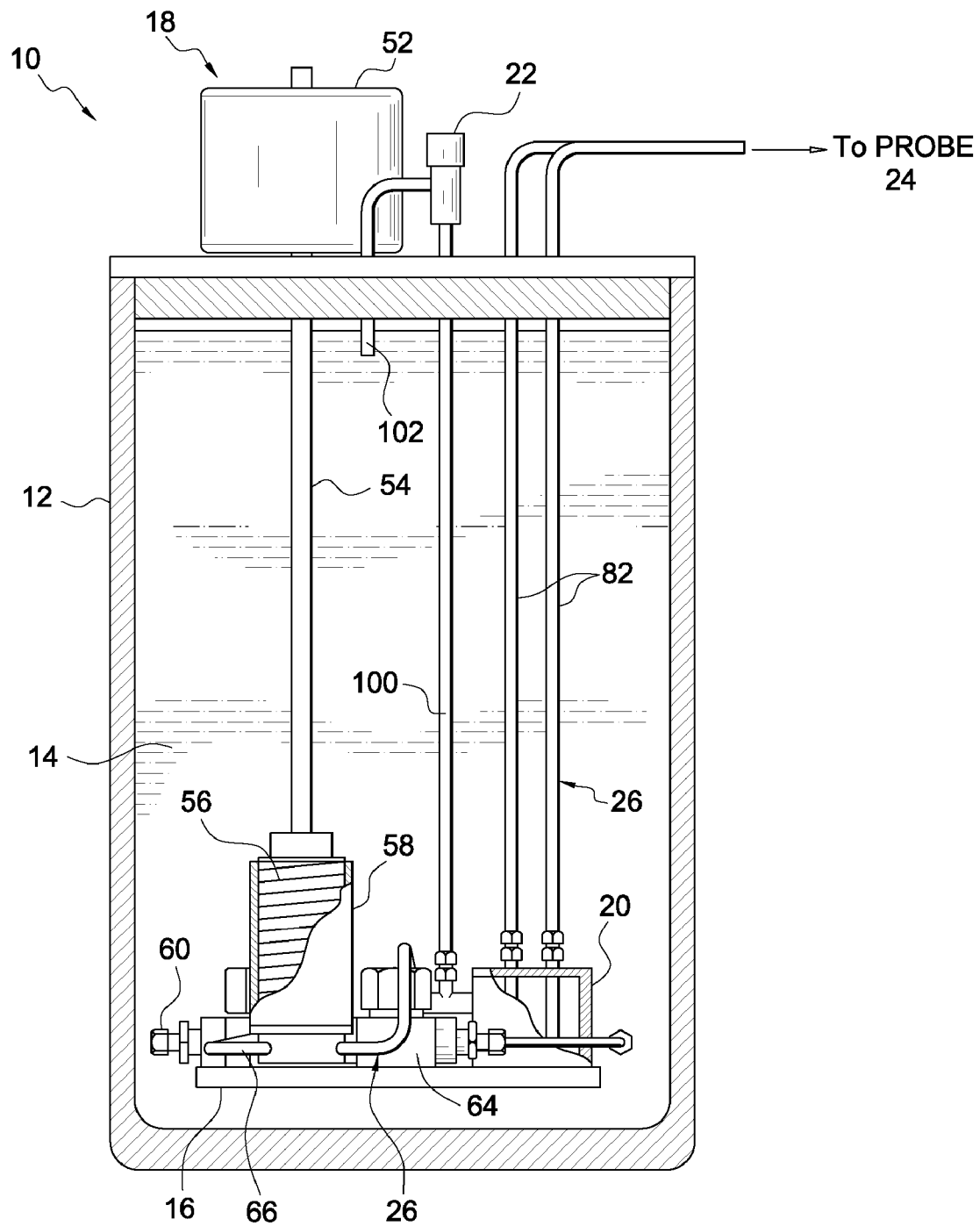
FIG. 1 illustrates a system in accordance with an embodiment of the present invention and includes a cross-sectional view through a container holding cryogen.
Figure 2:
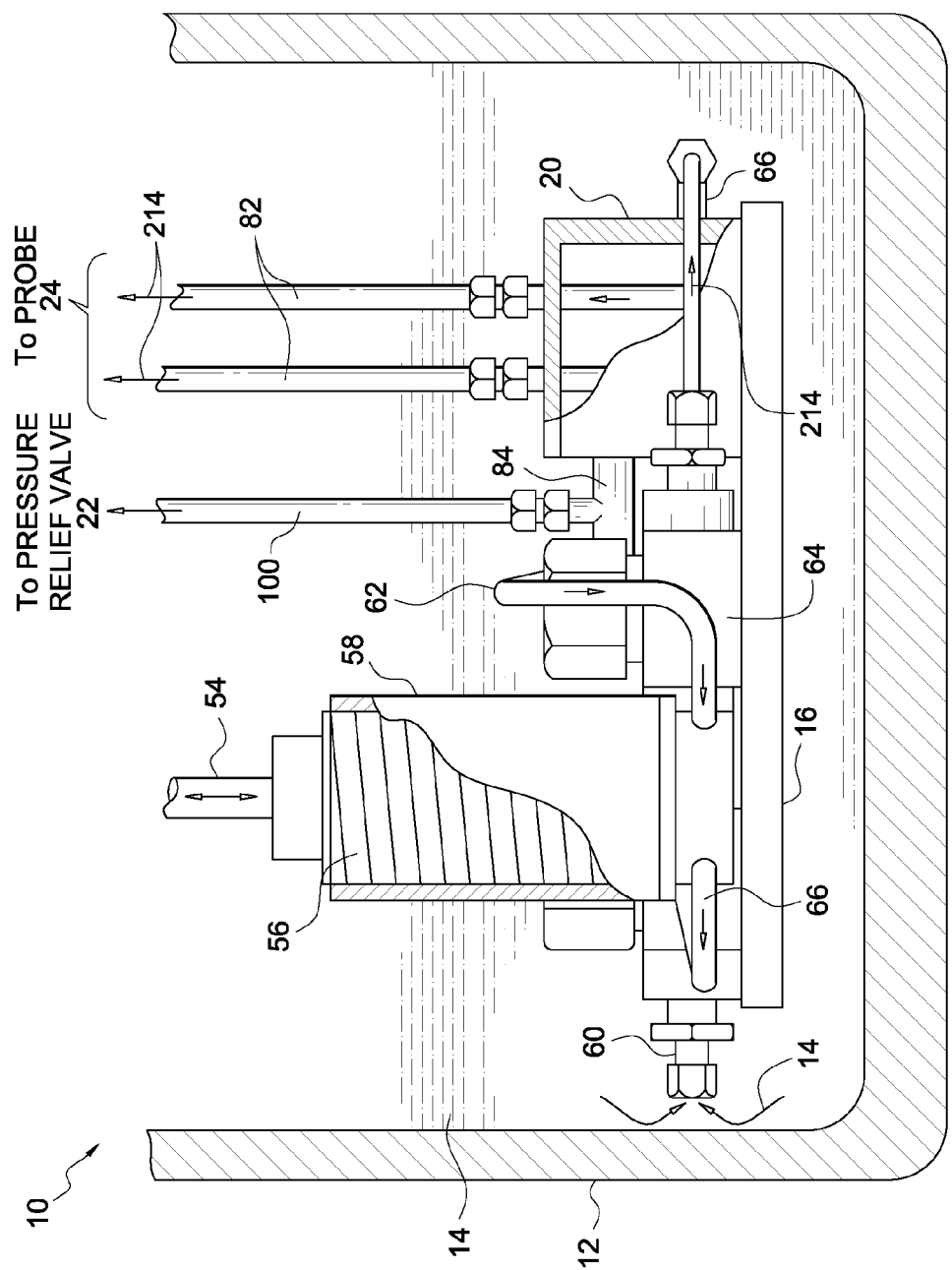
FIG. 2 is an enlarged, elevational view of the container of FIG. 1 and its contents.
Figure 3:
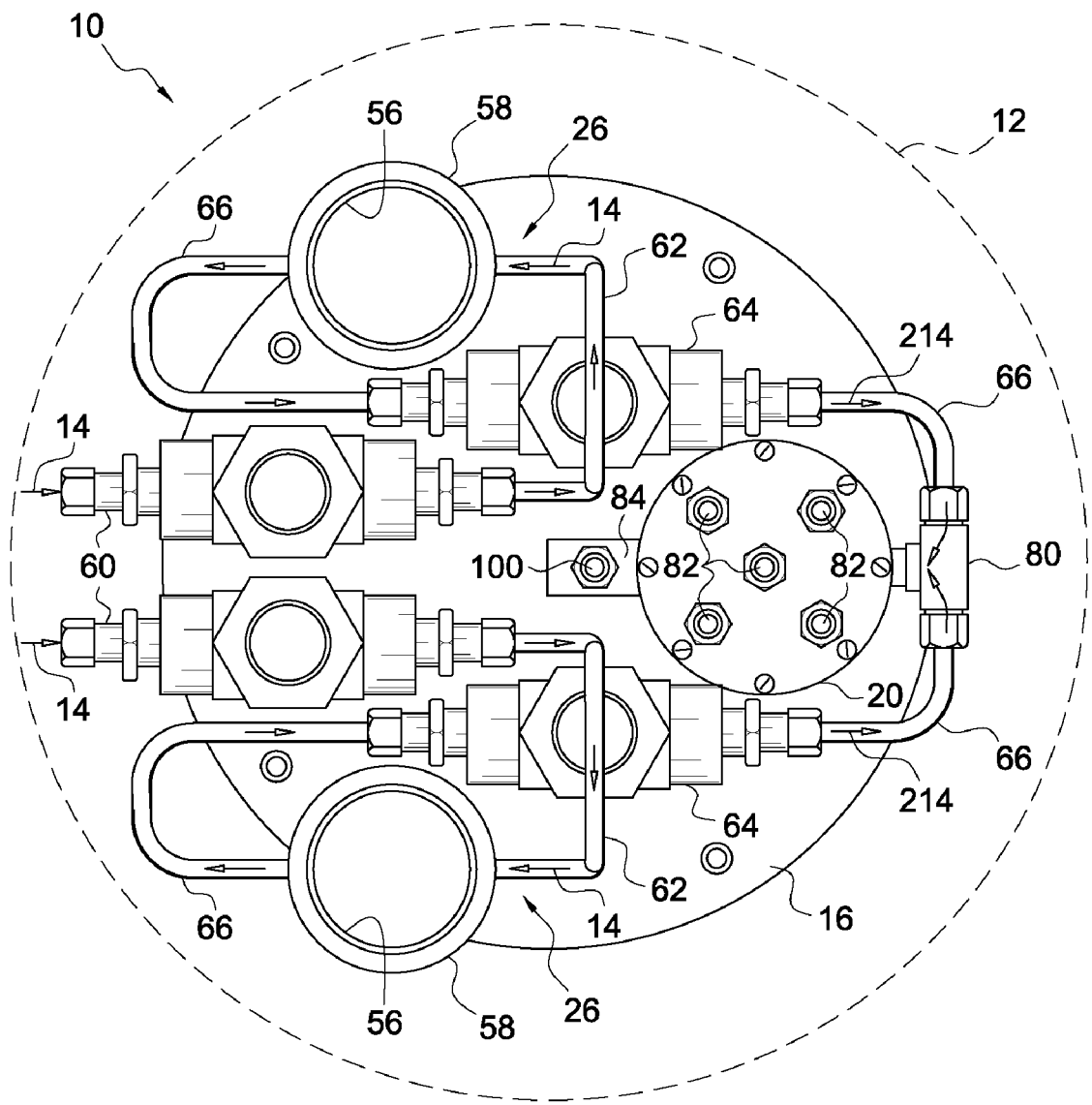
FIG. 3 is an enlarged, top view of the assembly within the container of FIG. 1.
Figure 4:
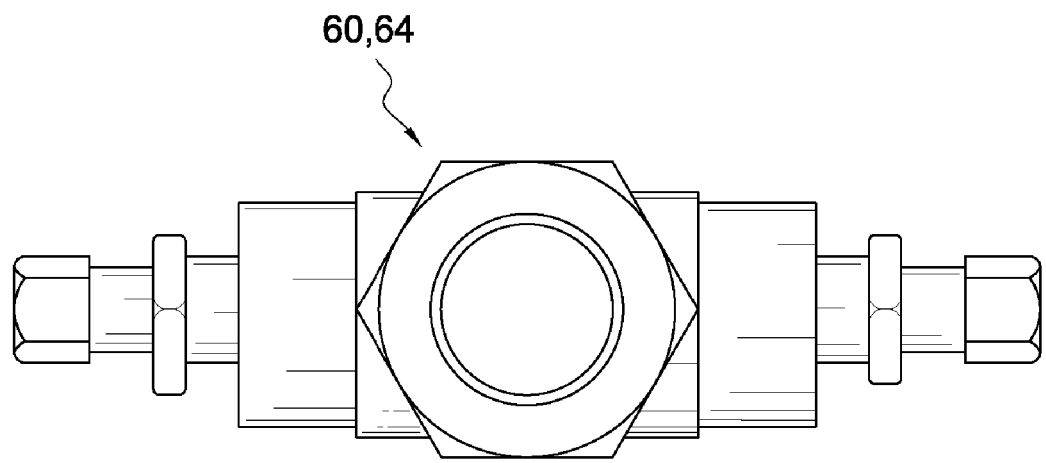
FIG. 4 is a top view of a valve used in the system illustrated in FIGS. 1-3.
Figure 5:
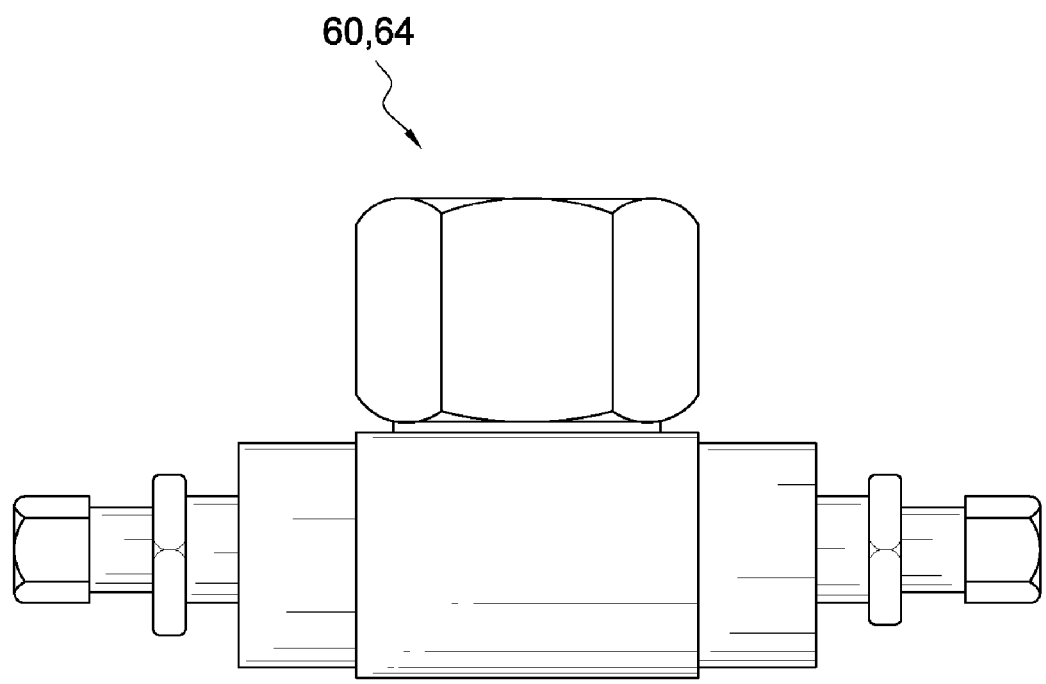
FIG. 5 is an elevational view of the valve of FIG. 4.
Figure 6:
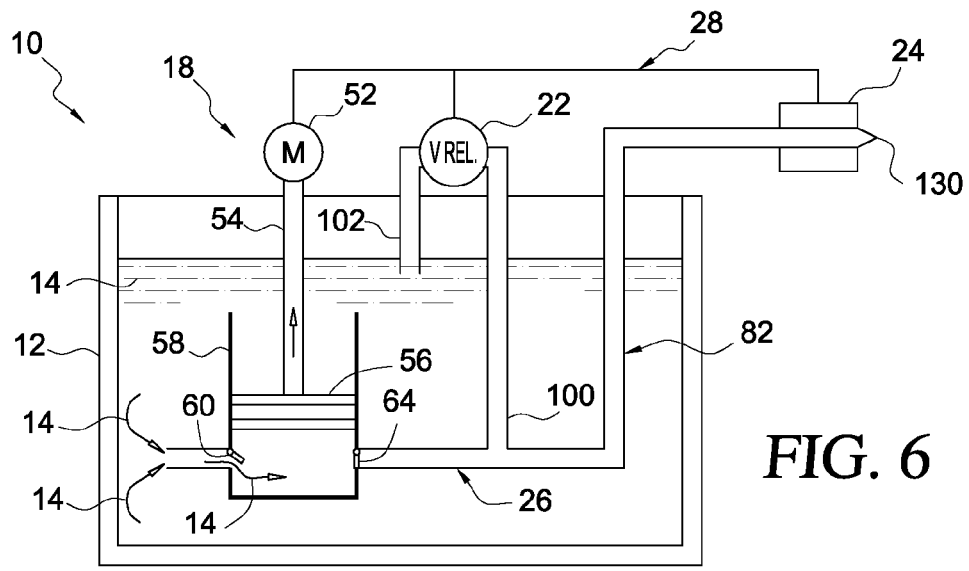
FIG. 6 is a schematic view of the system illustrated in FIG. 1 and showing the system as the bellows pulls cryogen within the cylinder.
Figure 7:
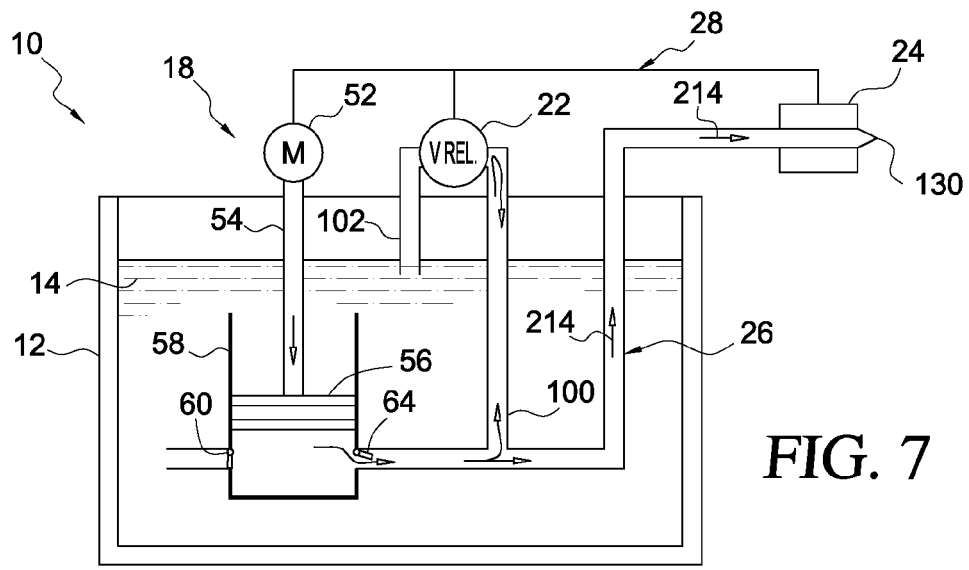
FIG. 7 is a schematic view similar to FIG. 6 but showing the system as the bellows initially pushes cryogen to the probe.
Figure 8:
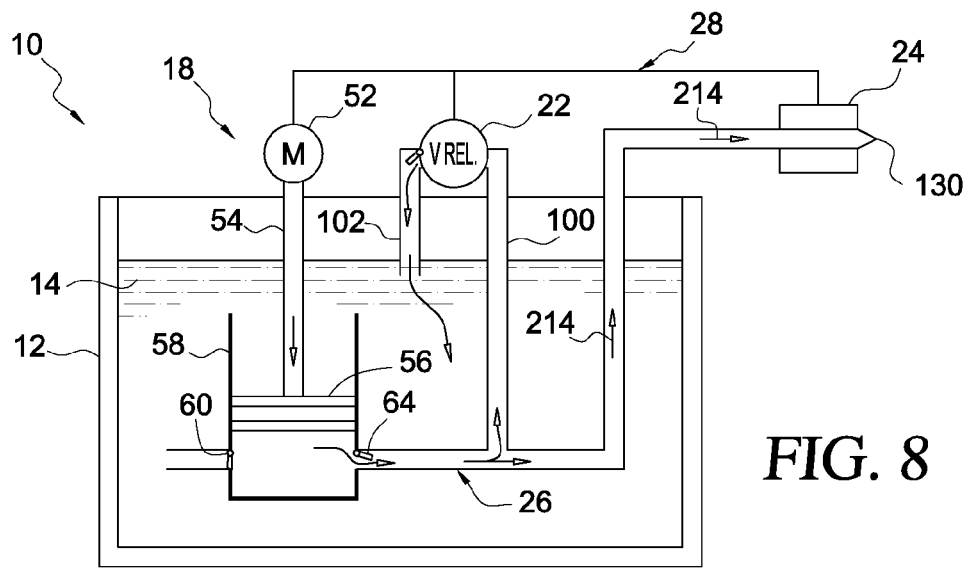
FIG. 8 is a schematic view similar to FIGS. 6 and 7 but showing the system as the bellows pushes cryogen to the probe and with the pressure relief valve activated to control the fluid pressure.

FIGS. 1-8 illustrate a preferred embodiment of a cryogenic pump, system, and method according to the present invention. The system 10 provides instantaneous sub-cooling of liquid cryogen 14, thereby creating a cryogen state characterized by an excess capacity to absorb heat without boiling. By manipulating the pressure relationships in the plumbing circuit 26, sub-cooled liquid 214 is transported to the distal cryoprobe tip 130 in 1-20 seconds allowing near instantaneous freezing at the probe tip 130. This rate of cooling is faster and the attainable low temperature is lower than comparable Joule-Thompson-based cryogenic devices.

The illustrated system 10 includes a container or dewar 12 containing cryogen 14, such as liquid nitrogen. A support 16 is positioned within the container 12 and submerged within the cryogen 14. A pump 18 is coupled to the container 12 such that the piston 56, illustrated in the form of a bellows, is also submerged within the cryogen 14. By way of a conduit system 26, the bellows 56 is fluidly coupled to an output manifold 20, a pressure release valve 22, and a surgical probe 24. A control system 28 monitors the temperature of the probe tip 130 and adjusts the system components as necessary to maintain the desired temperature at probe tip 130.

The container 12 is of substantially conventional design, except that it is appropriately adapted to support pump 18. Pump 18 includes a linear drive motor 52 mounted outside the container 12 and, preferably mounted to the top of the container 12. A drive shaft 54 extends down from the motor 52, through the cryogen 14 and couples to the bellows 56. The bellows 56 is appropriately constructed to fit within a cylinder 58. Bellows 56 is preferably formed from stainless steel. Also, although the figures illustrate a system 10 with two bellows 56, any appropriate number of bellow systems may be employed. The cylinder 58 has a one-way inlet valve 60 coupled to an inlet conduit 62, and a one-way outlet valve 64 coupled to an outlet conduit. The cylinder 58 and bellows 56 assembly is rigidly secured to the support 16 along with manifold 20.

Manifold 20 has an inlet conduit 80 fluidly coupled to the outlet valves 64 of the bellows 56. Manifold 20 also has outlet conduits 82 fluidly coupled to the probe 24. Although five outlet conduits 82 are illustrated it should be understood that the number of outlet conduits 82 is dependent on the system requirements, and that more or fewer outlet conduits 82 may be used. The manifold 20 also has an outlet port 84 for coupling with the pressure relief valve 22.

Pressure relief valve 22 is preferably mounted outside the container 12 and is coupled to the manifold by inlet conduit 100. The valve 22 also has an outlet conduit that leads back into the cryogen 14 in container 12 to return, to the container 12, the cryogen 14 that has been released from the conduit system 26 to lower the pressure as desired.

The surgical apparatus illustrated is shown as probe 24 with its corresponding tip 130 and is intended to represent any appropriate cryosurgical device, including probe tips, such as those known in the prior art. Examples of prior art probes are disclosed in the patents incorporated herein as set forth above.

Thus, the illustrated embodiment includes a reciprocating stainless steel bellows pump 18 that operates while submerged in liquid cryogen 14 and that causes instantaneous sub-cooling of the liquid cryogen 14 during the compression stroke of the bellows 56, thereby creating a cryogen state characterized by an excess capacity to absorb heat without boiling. Further, by manipulating the pressure relationships in the plumbing circuit 26, sub-cooled liquid 214 is transported to the distal cryoprobe tip 130 in 1-20 seconds allowing near instantaneous freezing at the probe tip 130.

In the illustrated embodiment, one or more stainless steel bellows "pistons" 56 are driven by a surface mounted linear drive system 52 capable of pressure regulation. The reciprocating action of each bellows piston 56 a) sequentially produces a negative pressure to draw in liquid cryogen 14 on the fill stroke through a one-way check valve 60 and b) sequentially discharge liquid cryogen 214 at a prescribed pressure profile out through a second one-way check valve 64 to a pressure manifold 20 connected to the probe 24 plumbing circuitry. The preferred, prescribed profile is a range of between 250 pounds per square inch (psi) and 400 pounds per square inch (psi).

The pressure pulse profile establishes an initial high, transient pressure spike that causes a colligative-based sub-cooling of the liquid cryogen 14, which establishes a boiling point differential of approximately 30-40 degrees Celsius, thereby establishing an excess temperature capacity (the level of temperature rise that can be allowed before boiling of the cryogen 14) supporting the instantaneous distribution of sub-cooled cryogen 214 in the plumbing circuit 26. Following the transient pressure spike, pressure is reduced to a base level to sustain the desired rate of ice growth a the distal end of the circuit, that is, at the probe 24. Conventional control system technology can be employed in controlling the interaction between the probe 24 and the pressure relief valve 22 and/or the pump 18, that is, in producing the control system 28.

Pressure relief and control is provided by an appropriately designed pressure transducer-valve interface 22 outside the cryogen-containing dewar 12.

Thus, while the invention has been disclosed and described with reference with a limited number of embodiments, it will be apparent that variations and modifications may be made thereto without departure from the spirit and scope of the invention and various other modifications may occur to those skilled in the art. Therefore, the following claims are intended to cover modifications, variations, and equivalents thereof.

The invention claimed is:

1. A cryosurgical system, comprising:
   a container having cryogen within said container;
   at least one cryoprobe outside said container for use in cryosurgical procedures; and,
   a pump assembly being connectable to said at least one cryoprobe, said pump assembly comprising:
      a driving mechanism coupled to an elongated drive shaft; and,
      a bellows coupled to said drive shaft and being submersed in cryogen, said bellows formed from metal;
      said pump assembly being an open loop system, cryogen not being returned to said cryoprobes,
         wherein said pump assembly provides a pressure to said at least cryoprobe greater than or equal to 250 pounds per square inch (psi).

2. A system according to claim 1, wherein said cryogen is nitrogen.

3. A system according to claim 1, wherein said cryogen is nitrogen.

4. A pump assembly for a cryosurgical system, comprising:
   a driving mechanism coupled to an elongated drive shaft; and,
   a bellows coupled to said drive shaft and adapted to be submersed in cryogen, said bellows formed from metal;
   a supply manifold having a plurality of ports for connection to cryoprobes, said pump assembly being an open loop system, cryogen not being returned to said cryoprobes,
      wherein said pump assembly provides a pressure to said cryoprobes greater than 250 pounds per square inch (psi).

5. A method of delivering cryogen to a surgical instrument, comprising:
   providing a container having cryogen within the container;
   providing a pump having a piston within a cylinder, said piston being submerged within the cryogen within said container;
   providing a surgical instrument outside the container for use in cryosurgical procedures;
   providing a system of conduits fluidly interconnecting the piston and the surgical instrument permitting the cryogen to be forced from the piston to the surgical instrument upon activation of the piston;
   activating the piston to pull cryogen within the cylinder; and,
   activating the piston to pull the cryogen from the cylinder to the surgical instrument to an initial predetermined pressure greater than 250 pounds per square inch (psi),
   wherein said system of conduits comprises an open loop system, cryogen not being returned to said instrument.

* * * * *